(12) United States Patent
Hassiepen et al.

(10) Patent No.: US 8,569,250 B2
(45) Date of Patent: *Oct. 29, 2013

(54) ORGANIC COMPOUNDS

(75) Inventors: Ulrich Hassiepen, Lörrach (DE);
Matthias Kittelmann, Freiburg (DE)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/560,421

(22) Filed: Jul. 27, 2012

(65) Prior Publication Data

US 2012/0295860 A1 Nov. 22, 2012

Related U.S. Application Data

(63) Continuation of application No. 12/744,510, filed as application No. PCT/EP2008/066159 on Nov. 25, 2008, now Pat. No. 8,252,751.

(60) Provisional application No. 61/004,846, filed on Nov. 30, 2007.

(51) Int. Cl.
*A61K 31/7036* (2006.01)
*A61P 3/10* (2006.01)

(52) U.S. Cl.
USPC .......................................................... 514/33

(58) Field of Classification Search
None
See application file for complete search history.

(56) References Cited

FOREIGN PATENT DOCUMENTS

WO WO/0034241 A1 6/2000
WO WO/2005012249 A2 2/2005

OTHER PUBLICATIONS

He, H. et al., Drug Metabolism and Disposition, "Absorption, Metabolism, and Excretion of [14C]Vildagliptin, a Novel Dipeptidyl Peptidase 4 Inhibitor, in Humans", 2009, vol. 37, No. 3, pp. 536-544 (referred to as He et al. 1).

He, H. et al., Drug Metabolism and Disposition, "Disposition of Vildagliptin, a Novel Dipeptidyl Peptidase 4 Inhibitor, in Rats and Dogs", 2009, vol. 37, No. 3, pp. 545-554 (referred to as He et al. 2).

*Primary Examiner* — Shaojia Jiang
*Assistant Examiner* — Bahar Craigo
(74) *Attorney, Agent, or Firm* — Daniel Woods

(57) ABSTRACT

A method of inhibiting dipeptidyl peptidase-IV comprising administering to a mammal in need of such treatment a therapeutically effective amount of a compound of formulae (I A), (I B), (X A), (X B), (Y A) or (Y or B),
wherein R' represents

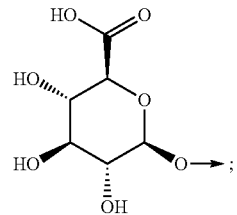

and R" represents hydrogen, hydroxy, $C_1$-$C_7$alkoxy, $C_1$-$C_8$-alkanoyloxy, or $R_5R_4N$—CO—O—, where $R_4$ and $R_5$ independently are $C_1$-$C_7$alkyl or phenyl which is unsubstituted or substituted by a substitutent selected from $C_1$-$C_7$alkyl, $C_1$-$C_7$alkoxy, halogen and trifluoromethyl and where $R_4$ additionally is hydrogen; or $R_4$ and $R_5$ together represent $C_3$-$C_6$alkylene,
in free form or in form of a pharmaceutically acceptable acid addition salt.

4 Claims, No Drawings

ORGANIC COMPOUNDS

This application is a continuation application of Ser. No. 12/744,510, filed May 25, 2010, which is a National Phase application of PCT/EP/2008/066159, filed Nov. 25, 2008, which claims benefit of Provisional Application No. 61/004,846, filed Nov. 30, 2007, which in their entirety are herein incorporated by reference.

The present invention provides new dipeptidyl peptidase-IV (DPP-IV) inhibitors which are effective in treating conditions mediated by DPP-IV. It was discovered that DPP-IV is responsible for inactivating glucagon-like peptide-1 (GLP-1). Since GLP-1 is a major stimulator of pancreatic insulin secretion and has direct beneficial effects on glucose disposal, DPP-IV inhibition appears to represent an attractive approach for treating conditions such as non-insulin-dependent diabetes mellitus (NIDDM).

The instant invention relates to a compound of formulae (I A), (I B), (X A), (X B), (Y A) or (Y B) (compounds of the invention)

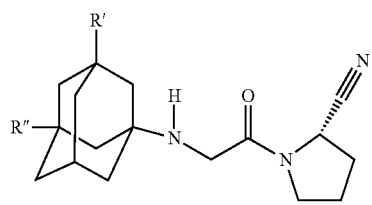
(IA)

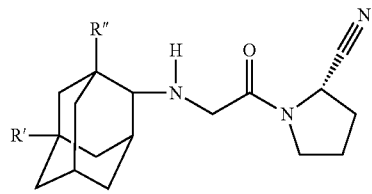
(IB)

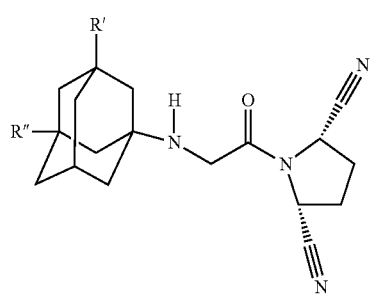
(XA)

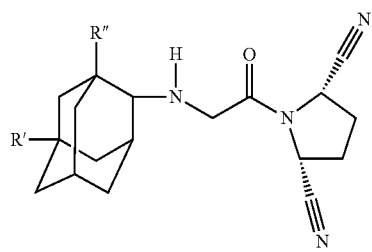
(XB)

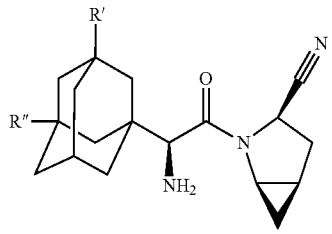
(YA)

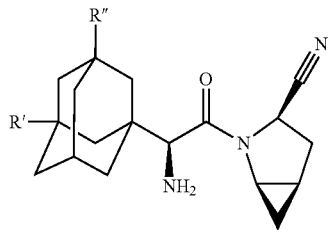
(YB)

wherein R' represents

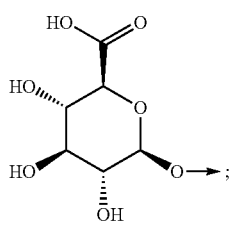

and R" represents hydrogen, hydroxy, $C_1$-$C_7$alkoxy, $C_1$-$C_8$-alkanoyloxy, or $R_5R_4N$—CO—O—, where $R_4$ and $R_5$ independently are $C_1$-$C_7$alkyl or phenyl which is unsubstituted or substituted by a substitutent selected from $C_1$-$C_7$alkyl, $C_1$-$C_7$alkoxy, halogen and trifluoromethyl and where $R_4$ additionally is hydrogen; or $R_4$ and $R_5$ together represent $C_3$-$C_6$alkylene;

in free form or in form of a pharmaceutically acceptable acid addition salt.

The invention also concerns a compound of formulae (I A), (I B), (X A), (X B), (Y A) or (Y B) as hereinabove described, wherein R" represents hydrogen.

In preferred embodiment, the compounds of formulae (I A), (I B), (X A), (X B), (Y A) or (Y B) as hereinabove described are in a substantially pure form.

The compounds of the invention can exist in free form or in acid addition salt form. Pharmaceutically acceptable (i.e., non-toxic, physiologically acceptable) salts are preferred, although other salts are also useful, e.g., in isolating or purifying the compounds of this invention. Although the preferred acid addition salts are the hydrochlorides, salts of methanesulfonic, sulfuric, phosphoric, citric, lactic and acetic acid may also be utilized.

The compounds of the invention may exist in the form of optically active isomers or diastereoisomers and can be separated and recovered by conventional techniques, such as chromatography.

Listed below are definitions of various terms used to describe this invention. These definitions apply to the terms as they are used throughout this specification, unless otherwise limited in specific instances, either individually or as part of a larger group.

The term "alkyl" refers to straight or branched chain hydrocarbon groups having 1 to 10 carbon atoms, preferably 1 to 7 carbon atoms, most preferably 1 to 5 carbon atoms. Exemplary alkyl groups include methyl, ethyl, propyl, isopropyl, n-butyl, t-butyl, isobutyl, pentyl, hexyl and the like.

The term "alkanoyl" refers to alkyl-C(O)—.

The term "substituted adamantyl" refers to adamantyl, i.e. 1- or 2-adamantyl, substituted by one or more, for example two, substitutents selected from alkyl, —OR$_1$ or —NR$_2$R$_3$; where R$_2$ and R$_3$ are independently hydrogen, alkyl, (C$_1$-C$_8$-alkanoyl), carbamyl, or —CO—NR$_4$R$_5$; where R$_4$ and R$_5$ are independently alkyl, unsubstituted or substituted aryl and where one of R$_4$ and R$_5$ additionally is hydrogen or R$_4$ and R$_5$ together represent C$_2$-C$_7$alkylene.

The term "aryl" preferably represents phenyl. Substituted phenyl preferably is phenyl substituted by one or more, e.g. two, substitutents selected from e.g. alkyl, alkoxy, halogen and trifluoromethyl.

The term "alkoxy" refers to alkyl-O—.

The term "halogen" or "halo" refers to fluorine, chlorine, bromine and iodine.

The term "alkylene" refers to a straight chain bridge of 2 to 7 carbon atoms, preferably of 3 to 6 carbon atoms, most preferably 5 carbon atoms.

The term "substantially pure" is understood in the context of the present invention to mean substantially free of biological material such as found in the blood, especially less than 10%, preferably less than 1%, and most preferably free of such biological material.

The compounds of the invention may be prepared e.g. by a process which comprises coupling a reactive (2-cyanopyrrolidino)carbonylmethylene compound with an appropriate substituted amine; more particularly, for the preparation of the compounds of formula I, it comprises reacting a compound of formula II

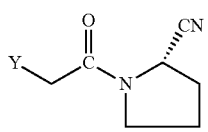
II wherein Y is a reactive group (preferably a halogen such as bromine, chlorine or iodine) with a compound of formula III

NH$_2$(CH$_2$)$_n$—R    III wherein R is as defined above, and recovering the resultant compound of formulae (I A), (I B), (X A), (X B), (Y A) or (Y B), in free form or in acid addition salt form.

Alternative processes to prepare precursors of the compounds of formula YA or YB are described in the patent application WO 01/068603, or WO 05/095339 for the compounds of formula XA or XB. The below described process can be used to obtain the O-glucuronide form of the compounds described in the patent application WO 01/068603, or WO 05/095339 and wherein R' is —OH.

The R' moiety can be attached to the chemical structure by any of the method well known by the person skilled in the art or by the process described herein after for the structures of the chemical formula IA or IB. Via preparative bioconversion using rat liver homogenate as the catalyst, the O-glucuronide of vildagliptin have been prepared as described herein after.

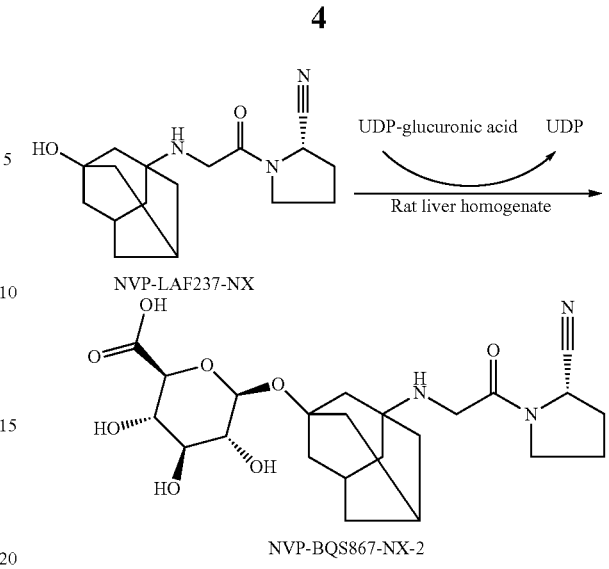

Vildagliptin (NVP-LAF237-NX or Galvus®) is a new oral hypoglycemic (anti-diabetic) drug of the dipeptidyl peptidase-4 (DPP-4) inhibitor class currently undergoing regulatory review by the U.S. FDA. The applicant has surprisingly discovered that the O-glucuronide of vildagliptin (Figure AA) remains as active as vildagliptin. The applicant has surprisingly discovered that the O-glucuronide of vildagliptin in addition to be equally potent to vildagliptin at inhibiting the DPP-4 enzyme, is less potent at inhibiting DPP-8 or DPP-9 enzymes. Its particularly unexpected that substituting the adamantly group of a DPP-4 inhibitors would provide improved pharmacological profile. The O-glucuronide of vildagliptin can provide further pharmacokinetic or pharmacological advantages e.g. less side effects, better bioavailability.

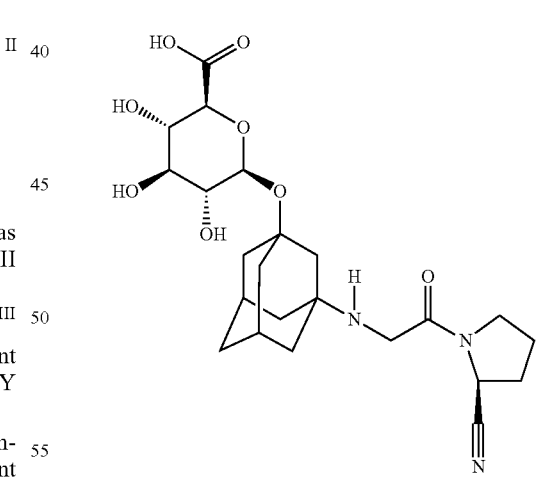

FIG. AA

In a most preferred embodiment, the O-glucuronide of vildagliptin (Figure AA) is in a substantially pure form.

The process of the invention may be effected in conventional manner. For example, the compound of formula II is reacted with 1 to 3 equivalents, preferably 3 equivalents of a primary amine of formula III. The reaction is conveniently conducted in the presence of an inert, organic solvent, such as methylene chloride or a cyclic ether such as tetrahydrofuran. The temperature preferably is of from about 0° to about 35° C., preferably between about 0° and about 25° C.

The compounds of the invention may be isolated from the reaction mixture and purified in conventional manner, e.g. by chromatography.

The starting materials may also be prepared in conventional manner. The compounds of formula II may be prepared by the following two-step reaction scheme:

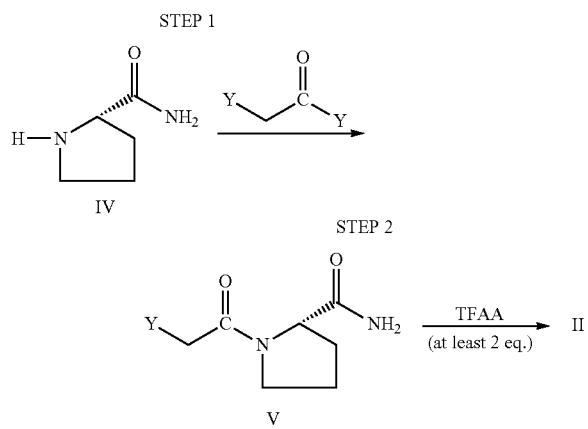

Step 1 involves the reaction of the pyrrolidine of formula IV with a slight molar excess of a haloacetylhalide such as bromoacetylbromide or chloroacetylchloride and a base such as potassium carbonate or triethylamine. The reaction conveniently is conducted in the presence of an inert, organic solvent, such as tetrahydrofuran or a chlorinated, aliphatic hydrocarbon such as methylene chloride, at a temperature of from about 0° to about 25° C., preferably at a temperature between about 0° and about 15° C.

Step 2 concerns the dehydration of the compound of formula V, prepared in Step 1, with 1 to 2 equivalents of trifluoroacetic anhydride (TFAA). The dehydration preferably is conducted in the presence of an inert, organic solvent such as tetrahydrofuran or a chlorinated, aliphatic hydrocarbon such as methylene chloride, at a temperature of from about 0° to about 25° C., preferably at a temperature between about 0° and about 15° C.

Insofar as its preparation is not particularly described herein, a compound used as starting material is known or may be prepared from known compounds in known manner or analogously to known methods or analogously to methods described in the Example.

For example, the primary amine compounds of formula III are known and may be prepared by procedures documented in the literature, for example, Khim.-Farm. Zh. (1986), 20(7), 810-15.

Finally, compounds of the invention are either obtained in the free form, or as a salt thereof if salt forming groups are present.

Compounds of the invention having basic groups can be converted into acid addition salts, especially pharmaceutically acceptable acid addition salts. These are formed, for example, with inorganic acids, such as mineral acids, for example sulfuric acid, a phosphoric or hydrohalic acid, or with organic carboxylic acids. Preferred are salts formed with hydrochloric acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The instant invention also includes pharmaceutical compositions, for example, useful in inhibiting DPP-IV, comprising a pharmaceutically acceptable carrier or diluent and a therapeutically effective amount of a compound of formula I, or a pharmaceutically acceptable acid addition salt thereof.

In still another embodiment, the instant invention provides a method of inhibiting DPP-IV comprising administering to a mammal in need of such treatment a therapeutically effective amount of a compound of the invention, or a pharmaceutically acceptable acid addition salt thereof.

In a further embodiment, the instant invention provides a method of treating conditions mediated by DPP-IV inhibition comprising administering to a mammal in need of such treatment a therapeutically effective amount of a compound of the invention above, or a pharmaceutically acceptable acid addition salt thereof.

The present invention also relates to the use of a compound according to the instant invention or a pharmaceutically acceptable salt thereof e.g. for the manufacture of a medicament for the prevention or treatment of diseases or conditions associated with elevated levels of DPP-IV.

As indicated above, all of the compounds of formulae (IA), (I B), (X A), (X B), (Y A) or (Y B), and their corresponding pharmaceutically acceptable acid addition salts, are useful in inhibiting DPP-IV. The ability of the compounds of the invention, and their corresponding pharmaceutically acceptable acid addition salts, to inhibit DPP-IV may be demonstrated employing the Caco-2 DPP-IV Assay which measures the ability of test compounds to inhibit DPP-IV activity from human colonic carcinoma cell extracts. The human colonic carcinoma cell line Caco-2 was obtained from the American Type Culture Collection (ATCC HTB 37). Differentiation of the cells to induce DPP-IV expression was accomplished as described by Reisher, et al. in an article entitled "Increased expression of intestinal cell line Caco-2" in Proc. Natl. Acad. Sci., Vol. 90, pgs. 5757-5761 (1993). Cell extract is prepared from cells solubilized in 10 mM Tris HCl, 0.15 M NaCl, 0.04 t.i.u. aprotinin, 0.5% nonidet-P40, pH 8.0, which is centrifuged at 35,000 g for 30 min. at 4° C. to remove cell debris. The assay is conducted by adding 20 µg solubilized Caco-2 protein, diluted to a final volume of 125 µl in assay buffer (25 mM Tris HCl pH 7.4, 140 mM NaCl, 10 mM KCl, 1% bovine serum albumin) to microtiter plate wells. After a 60 min. incubation at room temperature, the reaction is initiated by adding 25 µl of 1 mM substrate (H-Alanine-Proline-pNA; pNA is p-nitroaniline). The reaction is carried out at room temperature for 10 minutes after which time a 19 µl volume of 25% glacial acetic acid is added to stop the reaction. Test compounds are typically added as 30 µl additions and the assay buffer volume is reduced to 95 µl. A standard curve of free p-nitroaniline is generated using 0-500 µM solutions of free pNA in assay buffer. The curve generated is linear and is used for interpolation of substrate consumption (catalytic activity in nmoles substrate cleaved/min). The endpoint is determined by measuring absorbance at 405 nm in a Molecular Devices UV Max microtiter plate reader.

The potency of the test compounds as DPP-IV inhibitors, expressed as $IC_{50}$, is calculated from 8-point, dose-response curves using a 4-parameter logistic function.

The ability of the compounds of the invention, and their corresponding pharmaceutically acceptable acid addition salts, to inhibit DPP-IV may also be demonstrated by measuring the effects of test compounds on DPP-IV activity in human and rat plasma employing a modified version of the assay described by Kubota, et al. in an article entitled "Involvement of dipeptidylpeptidase IV in an in vivo immune response" in Clin. Exp. Immunol., Vol. 89, pgs. 192-197 (1992). Briefly, 5 μl of plasma are added to 96-well flat-bottom microtiter plates (Falcon), followed by the addition of 5 μl of 80 mM $MgCl_2$ in incubation buffer (25 mMHEPES, 140 mM NaCl, 1% RIA-grade BSA, pH 7.8). After a 60 min. incubation at room temperature, the reaction is initiated by the addition of 10 μl of incubation buffer containing 0.1 mM substrate (H-Glycine-Proline-AMC; AMC is 7-amino-4-methylcoumarin). The plates are covered with aluminum foil (or kept in the dark) and incubated at room temperature for 20 min. After the 20 min. reaction, fluorescence is measured using a CytoFluor 2350 fluorimeter (Excitation 380 nm Emission 460 nm; sensitivity setting 4). Test compounds are typically added as 2 μl additions and the assay buffer volume is reduced to 13 μl. A fluorescence-concentration curve of free AMC is generated using 0-50 μM solutions of AMC in assay buffer. The curve generated is linear and is used for interpolation of substrate consumption (catalytic activity in nmoles substrate cleaved/min). As with the previous assay, the potency of the test compounds as DPP-IV inhibitors, expressed as $IC_{50}$, is calculated from 8-point, dose-response curves using a 4 parameter logistic function.

In view of their ability to inhibit DPP-IV, the compounds of the invention, and their corresponding pharmaceutically acceptable acid addition salts, are useful in treating conditions mediated by DPP-IV inhibition. Based on the above and findings in the literature, it is expected that the compounds disclosed herein are useful in the treatment of conditions such as non-insulin-dependent diabetes mellitus, arthritis, obesity, allograft transplantation and calcitonin-osteoporosis. In addition, based on the roles of glucagon-like peptides (such as GLP-1 and GLP-2) and their association with DPP-IV inhibition, it is expected that the compounds disclosed herein are useful for example, to produce a sedative or anxiolytic effect, or to attenuate post-surgical catabolic changes and hormonal responses to stress, or to reduce mortality and morbidity after myocardial infarction, or in the treatment of conditions related to the above effects which may be mediated by GLP-1 and/or GLP-2 levels.

More specifically, for example, the compounds of the invention, and their corresponding pharmaceutically acceptable acid addition salts, improve early insulin response to an oral glucose challenge and, therefore, are useful in treating non-insulin-dependent diabetes mellitus. The ability of the compounds of the invention, and their corresponding pharmaceutically acceptable acid addition salts, to improve early insulin response to an oral glucose challenge may be measured in insulin resistant rats according to the following method:

Male Sprague-Dawley rats that had been fed a high fat diet (saturated fat=57% calories) for 2-3 weeks were fasted for approximately 2 hours on the day of testing, divided into groups of 8-10, and dosed orally with 10 μmol/kg of the test compounds in CMC. An oral glucose bolus of 1 g/kg was administered 30 minutes after the test compound directly into the stomach of the test animals. Blood samples, obtained at various timepoints from chronic jugular vein catheters, were analyzed for plasma glucose and immunoreactive insulin (IRI) concentrations, and plasma DPP-IV activity. Plasma insulin levels were assayed by a double antibody radioimmunoassay (RIA) method using a specific anti-rat insulin antibody from Linco Research (St. Louis, Mo.). The RIA has a lower limit of detection of 0.5 μU/mL with intra- and inter-assay variations of less than 5%. Data are expressed as % increase of the mean of the control animals. Upon oral administration, each of the compounds tested amplified the early insulin response which led to an improvement in glucose tolerance in the insulin resistant test animals. The following results were obtained:

The precise dosage of the compounds of the invention, and their corresponding pharmaceutically acceptable acid addition salts, to be employed for treating conditions mediated by DPP-IV inhibition depends upon several factors, including the host, the nature and the severity of the condition being treated, the mode of administration and the particular compound employed. However, in general, conditions mediated by DPP-IV inhibition are effectively treated when a compound of the invention, or a corresponding pharmaceutically acceptable acid addition salt, is administered enterally, e.g., orally, or parenterally, e.g., intravenously, preferably orally, at a daily dosage of 0.002-5, preferably 0.02-2.5 mg/kg body weight or, for most larger primates, a daily dosage of 0.1-250, preferably 1-100 mg. A typical oral dosage unit is 0.01-0.75 mg/kg, one to three times a day. Usually, a small dose is administered initially and the dosage is gradually increased until the optimal dosage for the host under treatment is determined. The upper limit of dosage is that imposed by side effects and can be determined by trial for the host being treated.

The compounds of the invention, and their corresponding pharmaceutically acceptable acid addition salts, may be combined with one or more pharmaceutically acceptable carriers and, optionally, one or more other conventional pharmaceutical adjuvants and administered enterally, e.g., orally, in the form of tablets, capsules, caplets, etc. or parenterally, e.g., intravenously, in the form of sterile injectable solutions or suspensions. The enteral and parenteral compositions may be prepared by conventional means. Examples of suitable formulations comprising the compounds of the invention are described in the patent applications WO 2005/067976 or WO 2006/078593.

Thus the invention also concerns a pharmaceutical composition comprising a compound according to any of claims 1 to 4 or herein described compounds, in free form or in pharmaceutically acceptable acid addition salt form, together with at least one pharmaceutically acceptable carrier or diluent.

The pharmaceutical compositions according to the invention are those suitable for enteral, such as oral or rectal; transdermal and parenteral administration to mammals, including man, for the treatment of conditions mediated by DPP4 activity. Such conditions include impaired glucose tolerance, Type 2 diabetes and obesity.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by dipeptidyl peptidase-IV inhibition, preferably, impaired glucose tolerance, Type 2 diabetes and obesity.

The present invention also provides the use of a pharmaceutical compositions as described above for the treatment of conditions mediated by dipeptidyl peptidase-IV inhibition, preferably, impaired glucose tolerance, Type 2 diabetes and obesity, wherein the compound of the invention (as defined in any of claims 1 to 4) is administered in combination with another therapeutic agent, e.g. one or two additional agent, as hereinafter described.

The pharmaceutical compositions may contain a therapeutically effective amount of a compound of the invention as defined herein (e.g. in claims 1 to 4), either alone or in a combination with another therapeutic agent, e.g., each at an effective therapeutic dose as reported in the art. Such therapeutic agents include:
a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;
b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid bile acid binding resins such as cholestyramine; fibrates; nicotinic acid and other GPR109 agonists; cholesterol absorption inhibitors such as ezetimibe; CETP inhibitors (cholesterol-ester-transfer-protein inhibitors), and aspirin;
c) anti-obesity agents such as orlistat, sibutramine and Cannabinoid Receptor 1 (CB1) antagonists e.g. rimonabant; and
d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; □-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.
e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof.

In each case in particular in the compound claims and the final products of the working examples, the subject matter of the final products, the pharmaceutical preparations and the claims are hereby incorporated into the present application by reference to these publications and patent applications.

Thus the invention covers pharmaceutical compositions comprising;
i) a compound according to any of claims 1 to 4, and
ii) at least one compound selected from
    a) antidiabetic agents,
    b) hypolipidemic agents,
    c) anti-obesity agents,
    d) anti-hypertensive agents,
    e) agonists of peroxisome proliferator-activator receptors,
ii) one or more pharmaceutically acceptable carriers.

Other specific anti-diabetic compounds are described by Patel Mona in *Expert Opin Investig Drugs*, 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by dipeptidyl peptidase-IV inhibition, preferably, impaired glucose tolerance, Type 2 diabetes and obesity.

The compounds of the invention, and their corresponding pharmaceutically acceptable acid addition salts, may be formulated into enteral and parenteral pharmaceutical compositions containing an amount of the active substance that is effective for treating conditions mediated by DPP-IV inhibition, such compositions in unit dosage form and such compositions comprising a pharmaceutically acceptable carrier.

The compounds of the invention (including those of each of the subscopes thereof and each of the examples) may be administered in enantiomerically pure form (e.g., ee>98%, preferably >99%) or together with the R enantiomer, e.g., in racemic form. The above dosage ranges are based on the compounds of the invention (excluding the amount of the R enantiomer).

The following examples show representative compounds encompassed by this invention and their synthesis. However, it should be clearly understood that they are for purposes of illustration only.

I. EXAMPLE 1

Pyrrolidine, 1-[(3-hydroxy-1-adamantyl)amino]acetyl-2-cyano-, (S) (INN: vildagliptin) or NVP-LAF237

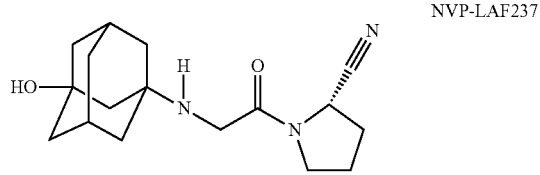 [SMILES: N#C[C@@H]1CCCN1C(=O)CNC12CC3CC(CC(O)(C3)C1)C2]

NVP-LAF237

A. 1-Aminoadamantane-3-ol

Slight modifications to the synthesis found in Khim.-Farm. Zh. (1986), 20(7), 810-15, may be used.

To a rapidly stirred, clear and colorless, ice-water chilled mixture of concentrated sulfuric acid 96% (210 mL; 3.943 mmol) and 65% nitric acid (21.0 mL; 217.0 mmol) is added 21.0 g (112.0 mmol) of 1-adamantylamine HCl (99%), in small portions over 30 minutes. Upon adamantylamine hydrochloride addition, slight bubbling occurs and the reaction is slightly exothermic. This bubbling, yellow solution is stirred at ice-water temperature for about 2 hours and then at room temperature for 30 hours. This clear, light yellow reaction is then poured into about 100 g of ice and the resulting solution is clear green-blue.

The solution is placed in an ice-water bath and allowed to stir for 30 minutes. Approximately 550 g of 89% pure KOH (8.74 mol) is then added in small portions over 45 minutes. During this addition, the reaction is exothermic; reaching 80° C. and producing copious amounts of brown $NO_2$ gas. By the end of the addition, the reaction is thick with white solids (both product and salts). The resulting white paste is then poured onto a buchner funnel/celite pad and washed with 1.2 L of $CH_2Cl_2$. The $CH_2Cl_2$ layer is then extracted from the water layer and dried over $Na_2SO_4$. The solution is then filtered and concentrated (rotovap/pump) to provide 1-aminoadamantane-3-ol as a white solid.

B. 1-Chloroacetyl-2-cyanopyrrolidine

To a mechanically stirred solution of 20.0 g (180.0 mmol) of chloroacetylchloride and 97 g (0.70 mmol) of potassium carbonate in 150 mL of tetrahydrofuran is added a solution of L-prolinamide 20.0 g (180.0 mmol) in 500 mL of tetrahydrofuran in a dropwise fashion over 45 minutes. This reaction is then mechanically stirred for an additional two hours at room temperature. The reaction is then filtered to remove potassium salts and the filtrate is dried over $Na_2SO_4$. The $Na_2SO_4$ is then removed via filtration and to this colorless filtrate is added trifluoroacetic anhydride (25.0 mL, 0.180 mmol) in one portion. The reaction is then magnetically stirred for 1 hour at room temperature and the resulting clear yellow/orange solution is concentrated via rotovap. The excess trifluoroacetic anhydride is removed by adding ethyl acetate to the concentrated oil and reconcentrating via rotovap. This removing operation is performed three times.

The resulting oil is partitioned between ethyl acetate and water. The product is then extracted into the ethyl acetate and the aqueous layer is then washed twice with ethyl acetate. The combined organic layers are then washed successively with water and brine dried over magnesium sulfate, filtered and concentrated to obtain 1-chloroacetyl-2-cyanopyrrolidine as a yellow solid.

C. Pyrrolidine, 1-[(3-hydroxy-1-adamantyl)amino]acetyl-2-cyano-, (S)

To a heterogeneous solution of the title A compound (1-aminoadamantane-3-ol (5.80 g, 34.7 mmol) in $CH_2Cl_2$ (68.0 mL) is added 9.6 g (69 mmol) of $K_2CO_3$. This heterogeneous mixture is then cooled in an ice-water bath and a solution of 3.0 g (17 mmol) of the title B compound (1-chloroacetyl-2-cyanopyrrolidine) dissolved in 25.0 mL of $CH_2Cl_2$ is added dropwise over a period of 30 minutes. The resulting mixture is stirred for 2 hours at 0° C. and at room temperature for 6 days. The reaction is then concentrated to obtain a yellow pasty material which is purified on silica gel employing a SIMS/Biotage Flash chromatography system and a 7% solution of methanol in methylene chloride as the eluent to yield the title compound in free base form as a white crystalline solid (melting point 138° C.-140° C., $^{13}$CNMR (ppm)=119.59).

A. D. Biocatalytic Synthesis of NVP-BQS867 (the O-glucuronide of Vildaoliptin) and NVP-BRU563 (the Labeled O-Glucuronide of Vildaqliptin).

The reaction scheme of the enzymatic glucuronidation of NVP-LAF237 under catalysis of rat liver homogenate is shown in FIG. 4-1.

Biotransformation of NVP-LAF237

(i) Figure I-1

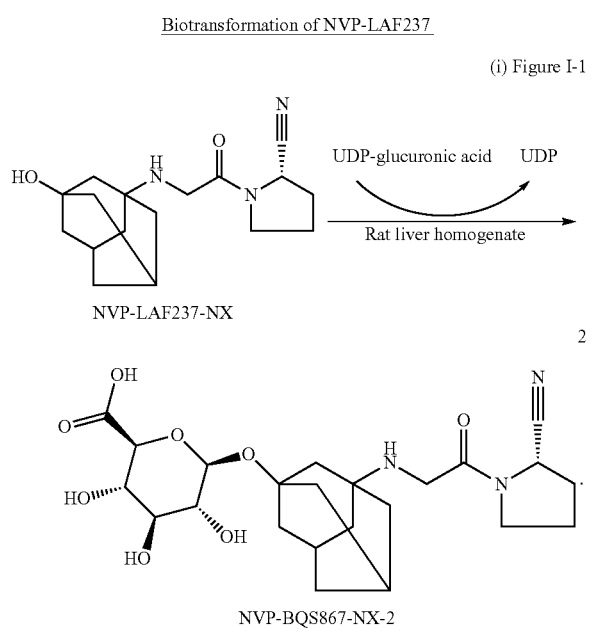

3. 1. Preparation of Rat Liver Homogenate

Two portions of 15 g and one of 11 g of frozen rat liver were defrosted and cut into small pieces. After addition of 0.5 volume equivalent of ice cold 0.9% NaCl solution to each portion of liver and mixing in a Dispomix blender, the tissue was homogenized in a "Potter S" Tissue Homogenizer (Braun Biotech Inc., Melsungen, Germany) under cooling in ice water by moving the teflon pistil 3 times up and down at 100% stirrer speed. The homogenate was filled up to a final weight of 81 g and centrifuged at 4-6° C. for 30 min at 10,000 rpm (=17,000×g) in a Beckmann Coulter centrifuge (Fullerton, Calif., USA) type Avanti J-HC equipped with a JA-10 rotor. The supernatant served as the enzyme source.

4. 2. Bioconversion on Preparative Scale

The conditions for glucuronidation of NVP-LAF237 (vildagliptin) on 340 mg scale were: NVP-LAF237 5 mM, UDP-glucuronate (Yamasa Co., Tokyo, JP) 20 mM, $MgCl_2$ 20 mM, HEPES, pH 8.5 160 mM, rat liver homogenate 20% v/v, total volume 224 ml, incubation for 5 h at 37° C. and further 14 h at 30° C. The reactions were performed in 50 ml Nunc tubes each filled with 20 ml of reaction mixture, which were shaken at 170 rpm on a microbiological lab shaker with 5 cm shaking radius.

The preparative reaction was stopped by addition of 224 ml of acetonitrile and mixing for 10 min at 20° C. After centrifugation for 15 min at 8000 rpm (rotor JA-10), the pellet was suspended in 50 ml of 50% v/v acetonitrile in deionized water and centrifuged again. The combined supernatants were concentrated to 50 ml under reduced pressure at 25° C. The turbid concentrate was centrifuged at 5000 rpm, and after filtering the supernatant through fiberglass it was subjected to preparative HPLC.

For glucuronidation of $[^{13}C_5\ ^{15}N]$ labeled NVP-LAF237 (50 mg scale), the biotransformation conditions were the same as for NVP-LAF237 on 340 mg scale except that the concentration of UDP-glucuronate was 80 mM, of rat liver homogenate 30% v/v, the filling volume of the Nunc tubes was 16.5 ml, the total volume 33 ml, the reaction time 4 h and the shaking speed 200 rpm.

The reaction was stopped by addition of 16.5 ml of acetonitrile to each tube, incubation for 15 min on ice and subsequent mixing. After centrifugation for 15 min at 17,000 rpm (rotor JA-10), the sediment was resuspended in 20 ml of 50% v/v acetonitrile in deionized water and centrifuged again. The combined supernatants were concentrated to 10 ml under reduced pressure at 30° C., again diluted to 25 ml final volume and centrifuged for final clarification. The pellet was resuspended with 5 ml of deionized water, and after centrifugation, the latter two supernatants were combined and subjected to preparative HPLC.

Measurement of Conversion/Analytical HPLC-DAD:

50 µl of a 19 h samples of the 340 mg batch of NVP-LAF237 and 25 µl of a 4 h sample of the batch with $[^{13}C_5\ ^{15}N]$ labeled NVP-LAF237 were each mixed with 200 µl of 50% acetonitrile in water and centrifuged in a Sigma 4K15C refrigerated centrifuge. The supernatant was analyzed by analytical $RP_{18}$—HPLC-DAD (HPLC-DAD 1100 series from Agilent Technologies, Basel, Switzerland; two connected columns of the type Chromolith Performance RP-18e 100× 4.6 mm with a Chromolith Guard Cartridge RP-18e 5×4.6 mm (Merck); flow 2 ml/min; mobile phase A: 3 mM aqueous $H_3PO_4$, mobile phase B: acetonitrile; gradient from 3% to 15% B in 5 min; DAD detection at 200-400 nm). Conversion was based on the UV-absorption peak areas at 205 nm of the glucuronide and NVP-LAF237.

5. E. Purification of the Metabolites a) a) NVP-BQS867-NX-2

A part (5 ml or approximately 10%) of bioconverted raw material was used for the preparation of batch NVP-BQS867-NX-2. To this volume 35 ml of aqueous 10 mM $NH_4Ac$ and 8 ml of methanol were added. The pH was adjusted to 7 with diluted acetic acid. This mixture was then used as injection solution for preparative liquid chromatography.

The preparative liquid chromatography-mass spectrometry system consisted of a Waters Autopurification system (Waters Corp. Milford, Mass., USA) with 2525 pump, 2767 sample manager, 2996 photodiode detector, 515 make-up pump, ZQ2000 mass spectrometer and MassLynx 4.0 and FractionLynx 4.0 software.

An Atlantis dC18, 5 µm, 19 mm×100 mm column (Waters) was employed; flow rate 20 ml/min; mobile phase A: aqueous 10 mM $NH_4Ac$, pH 7.0; mobile phase B: $CH_3CN/CH_3OH$ 4:1, 10 mM $NH_4Ac$; gradient program: 0 min. 5% B; 2 min. 5% B; 7 min. 20% B; 7.1-12 min. 95% B; 12.1-14 min 5% B; injection volume 1-5 ml. The column effluent was split, a very small part was mixed in-line with make-up liquid 2-propanol/$H_2O$/HCOOH 400:100:1 and introduced into the ion source of the mass spectrometer; the rest entered the DAD detector recording from 200-600 nm, and subsequently the sample manager for fraction collection.

The mass spectrometer was equipped with ESCi interface used in the positive ESI mode. A capillary voltage of 3 kV and a cone voltage of 30 V was applied; mass range 250-550 Da.

The target fraction was collected time-based from 5.3-6.7 min. Target fractions from 12 HPLC runs were combined, the organic solvent was removed under reduced pressure at 30° C., and the remaining solution freeze-dried at −80° C. and 0.2 mbar yielding 15 mg as almost colorless lyophilizate.

The purity was determined by HPLC-DAD and HPLC-MS (see section 2.2.2): Apart from salts (ammonium acetate) and water the batch NVP-BQS867-NX-2 had a purity of >97%.

b) b) NVP-BRU563-NX-1 (Stable Labeled Glucuronide)

An equal volume of 20 mM $NH_4Ac$ solution was added to the aqueous extract to form a $NH_4Ac$ concentration of 10 mM. This mixture was adjusted to pH 7.0 with diluted acetic acid and then used as injection solution for preparative liquid chromatography. The preparative liquid chromatography-mass spectrometry system was described in 2.1.3.1.

An Atlantis Prep dC18 OBD, 5 μm, 30 mm×150 mm column (Waters) was employed; flow rate 40 ml/min; mobile phase A: aqueous 10 mM NH$_4$Ac; mobile phase B: CH$_3$CN/CH$_3$OH 4:1+10 mM NH$_4$Ac, pH 7.0; gradient program: 0 min. 5% B; 2 min. 5% B; 7 min. 20% B; 7.1-12 min. 95% B; 12.1-14 min 5% B; injection volume 2-6 ml. The column effluent was split in the same way as described in 2.1.3.1.

The mass spectrometer was equipped with ESCi interface used in the positive ESI mode. A capillary voltage of 3 kV and a cone voltage of 30 V was applied; mass range 100-1000 Da.

The target fraction was collected time-based from 7.0-9.0 min. Target fractions from 12 HPLC runs were combined, the organic solvent was removed under reduced pressure at 30° C., and the remaining solution freeze-dried at −80° C. and 0.2 mbar yielding 63 mg as almost colorless lyophilizate.

The purity was determined by HPLC-DAD and HPLC-MS (see section 2.2.2): Apart from salts (ammonium acetate) and water the batch NVP-BRU563-NX-1 had a purity of >98%.

B. F. Analytics for Structure Identification

1. NMR Spectroscopy

The compounds were dissolved in 5 μl DMSO-d$_6$ and filled in a 1 mm diameter NMR tube. From NVP-BQS867, a 1D-$^1$H spectrum and 2D homo- and heteronuclear spectra (COSY, HSQC, HMBC, ROESY) were obtained. From NVP-BRU563, a $^1$H spectrum was measured. All spectra were recorded at 300° K on a Bruker DRX600 spectrometer, using a $^1$H {$^{13}$C, $^{15}$N} Microliterprobe. From NVP-BQS867, a $^{13}$C spectrum was measured on a BRUKER DRX600 spectrometer using a 5 mm $^{13}$C {$^1$H} Cryoprobe.

2. 2. HPLC-Mass Spectrometry

The liquid chromatograph consisted of a Waters HPLC Acquity (Waters) equipped with a Waters Acquity 2996 PDA detector. Column: Acquity HPLC BEH C18; 1.7 μm; 1.0×150 mm (Waters); flow rate 0.1 ml/min.; eluent A: H$_2$O/TFA 100:0.1; eluent B: acetonitrile/TFA 100:0.1; gradient: 0 min. 5% B; 1 min. 5% B, 11 min. 40% B; 13-16 min. 95% B; 30° C.; UV-detection: 200-350 nm, resolution 2.4 nm; injection volume 5 μl. The substance was dissolved in water/acetonitrile 9:1 at a concentration of approximately 0.3 mg/ml. Evaluation of the purity was done by UV at 210 nm as area-% of the desired peak. The column effluent was introduced directly into the ion source of the MS.

A TSQ Quantum AM mass spectrometer (Thermo, San Jose, Calif., USA) equipped with electrospray interface in the positive mode was used. It was operated with Xcalibur software version 2.0. A sheath gas setting of 25 units and auxiliary gas of 5 units was used and a spray voltage of 3 kV applied. The heated metal capillary was maintained at 300° C.; mass range 200 to 800 Da. MS/MS parameters: collision gas 1.5 mTorr argon; collision energy 25 V.

II. G. RESULTS

A. 1. Biocatalytic Synthesis

For the two preparative reactions analytical HPLC-DAD gave the following conversion values: 66% for the batch with 340 mg of NVP-LAF237 and 94% for the batch with [$^{13}$C$_5$ $^{15}$N] labeled NVP-LAF237 (50 mg).

2. Purification of the Glucuronides

As described in above section, 15 mg of O-glucuronide NVP-BQS867-NX-2 was obtained by preparative HPLC-MS from 5 ml of aqueous culture extract obtained from biotransformation. From the whole preparative reaction with 340 mg of NVP-LAF237, four batches of NVP-BQS867-NX (NX-1 to NX-4) were isolated with a total amount of 295 mg of O-glucuronide.

3. Structure Elucidation

The mass spectrum of NVP-BQS867-NX-2 shows a [M+H]$^+$ of 480.1 suggesting a molecular weight of 479. This is consistent with a glucuronide of NVP-LAF237. The MS/MS product ion spectrum shows the loss of glucuronide (m/z 304) as well as glucuronic acid (m/z 286).

The structure of NVP-BQS867-NX-2 (FIG. 3-1) was elucidated unambiguously on the basis of NMR spectroscopy. The major differences in the NMR spectra of NVP-BQS867 compared with NVP-LAF237 are mainly the resonances obtained from the glucuronide moiety. The $^1$H-(4.42 ppm) and the $^{13}$C shift (96.4 ppm) of the anomeric 1' resonance of the glucuronic acid indicated that the latter is attached to oxygen and not to nitrogen. An HMBC correlation from H-1' to C-3 and ROESY correlations from H-1' to H-2 and H-4 confirmed the structure shown in FIG. 3-1 unambiguously.

The interpretation of all NMR data and correlations lead to only one structure which is in accordance with the MS result (MW=479, m/z MH$^+$=480.1). A summary of all $^1$H— and $^{13}$C shifts and relevant homo- and heteronuclear correlations is shown in Table 3-1.

The compound NVP-BRU563-NX-3, biosynthesized from [U-pyrrolidin,cyano-$^{13}$C$_5$,pyrrolidin-$^{15}$N] labeled NVP-LAF237, showed identical spectral properties to NVP-BQS867-NX with the expected exceptions for the stable label: The MH$^+$ of 486.2 is 6 Da higher than that of NVP-BQS867-NX and in the MS/MS product ion spectrum some fragments are also shifted.

(i) Figure II-1 Structure of NVP-BQS867 with numbering scheme used in Table 3-1 and $^1$H spectrum Table II-1

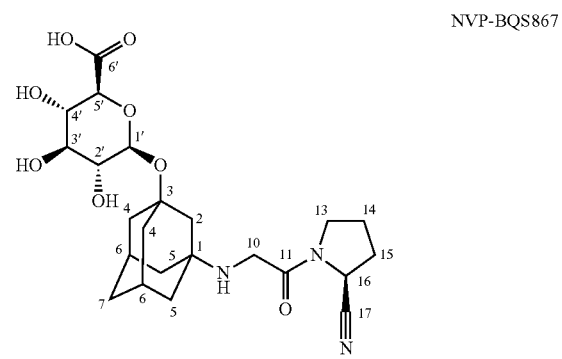

NVP-BQS867

(b) $^1$H- and $^{13}$C assignments for structure of NVP-BQS867

| Pos. | Group | $^1$H-shift | $^{13}$C-shift | HMBC correlation | NOE correlations |
|---|---|---|---|---|---|
| 1 | Cq | | 53.6 | H-10, H-2, H-5 | |
| 2 | CH$_2$ | 1.74, 1.60 | 46.6 | | H-1' |
| 3 | Cq | | 75.4 | H-1', H-2, H-4 | |
| 4 | 2× CH$_2$ | 1.70, 1.67, 1.60 | 41.9, 41.6 | | H-1' |
| 5 | 2× CH$_2$ | 1.55 | 41.4, 41.1 | | |
| 6 | 2× CH | 2.20 | 30.5, 30.6 | | |
| 7 | CH$_2$ | 1.48, 1.43 | 35.5 | | |
| 10 | CH$_2$ | 3.53, 3.49 | 43.5 | | |
| 11 | CO | | 170.9 | H-10 | |
| 13 | CH$_2$ | 3.64, 3.46 | 45.7 | | |
| 14 | CH$_2$ | 2.06, 1.99 | 25.2 | | |
| 15 | CH$_2$ | 2.20, 2.13 | 30.0 | | |
| 16 | CH | 4.76 | 47.2 | | |
| 17 | Cq | | 119.9 | H-16, H-15 | |
| 1' | CH | 4.42 | 96.4 | H-2', H-5' | H-2, H-4, H-2', H-3', H-5' |
| 2' | CH | 2.89 | 73.8 | | |
| 3' | CH | 3.15 | 77.4 | | |

Table II-1-continued

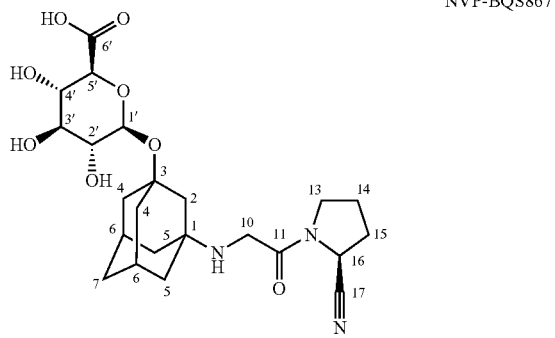

NVP-BQS867

(b) $^1$H- and $^{13}$C assignments for structure of NVP-BQS867

| Pos. | Group | $^1$H-shift | $^{13}$C-shift | HMBC correlation | NOE correlations |
|---|---|---|---|---|---|
| 4' | CH | 3.18 | 72.7 | | |
| 5' | CH | 3.41 | 74.4 | | |
| 6' | CO | | 172.6 | | |

Another preferred compound is:

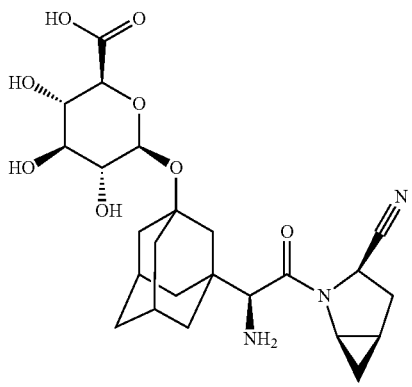

FIG. BB

In a most preferred embodiment, the compound of Figure BB is in a substantially pure form.

This O-glucuronide compound (Figure BB) can be obtained by adapting the herein described process. The process to obtain the starting compound from wherein R' is —OH is described in the patent application WO 01/068603, or WO 05/095339.

A salt can be the HCL salt. (HCl)=as hydrochloride. All HCl salts of final products are prepared by passing HCl gas through a 0.1 Molar solution of the free base in tetrahydrofuran until solution is clearly acidic followed by removal of the solvent (rotovap/pump).

The amino-adamantane starting materials are known in the literature or can be prepared as follows:

The manufacture of 3,5-dimethyl-1-adamantylamine is described in J. Med. Chem., 25; 1; 1982; 51-56.

The manufacture of 3-ethyl-1-adamantylamine is described in J. Med. Chem., 25; 1; 1982; 51-56.

3-Methoxy-1-adamantylamine can be prepared as follows:

To a stirred, ice-water chilled suspension of potassium hydride (0.680 gm; 5.95 mmol) in 15.0 ml of tetrahydrofuran is added a mixture of 1-aminoadamantane-3-ol (1.00 g; 5.95 mmol) and 15.0 ml of tetrahydrofuran dropwise over 30 minutes. The resulting mixture is then stirred for an addition 30 minutes and iodomethane (0.370 ml; 5.95 mmol) is then added dropwise over one minute. The resulting opaque white reaction is then stirred at room temperature for 18 hours. The mixture is then diluted with 50 ml of methylene chloride and filtered to remove the inorganic impurities. The filtrate is then concentrated and purified on silica gel employing a SIMS/Biotage apparatus and 19% methanol and 1% ammonium hydroxide in methylene chloride as eluent to yield 3-methoxy-1-adamantylamine as an opaque oil.

Synthesis of 3-[[(tertbutylamino)carbonyl]oxy]-1-aminoadamantane

To a mixture of 1-aminoadamantane-3-ol (5.00 g; 30.0 mmol) and potassium carbonate (6.20 g; 45 mmol) in 150 ml of tetrahydrofuran is added benzylchloroformate (4.70 g, 33.0 mmol) in dropwise fashion over a 10 minute period. The mixture is then stirred at room temperature for 2 h and then partitioned between ethyl acetate and water. The product is then extracted into the ethyl acetate and the aqueous layer is washed twice with ethyl acetate (100 ml). The combined organic layers are then washed successively with 100 ml of aqueous 2 N sodium hydroxide, water and brine, dried over sodium sulfate, filtered and concentrated (rotovap/pump) to provide 1-benzylcarbamoyladamantane-3-ol as a white solid in 85% yield.

To a clear solution of 1-benzylcarbamoyladamantane-3-ol (1.00 g: 3.32 mmol) and tert-butylisocyanate (380 µl, 3.32 mmol) in 30 ml of methylene chloride is syringe-added trimethylsilyl chloride (20.0 µl, 0.17 mmol). This reaction is then stirred at room temperature for 18 hours, concentrated (rotovap) and purified on silica gel employing a SIMS/Biotage apparatus and 20% ethyl acetate in hexane as eluent to yield 3-[[(tertbutylamino)carbonyl]oxy]-1-benzylcarbamoyladamantane as a white solid in quantitative yield.

To a mixture of 3-[[(tertbutylamino)carbonyl]oxy]-1-benzylcarbamoyladamantane (1.50 g, 3.75 mmol) and 10% palladium on carbon (400 mg) in ethanol (150 ml) in a 1-liter parr hydrogenation flask is added hydrogen (50 psi). This opaque black mixture is then shaken for 24 h. The reaction is then filtered through celite to remove the palladium catalyst and concentrated (rotovap/pump) to provide 3-[[(tertbutylamino)carbonyl]oxy]-1-aminoadamantane as a clear oil in 99% yield. The procedure for the synthesis of 4-[[[(methoxyphenyl)amino]carbonyl]oxy]-1-aminoadamantane is essentially the procedure of 3-[[(tertbutylamino)carbonyl]oxy]-1-aminoadamantane except in the second step where an equivalent of 4-methoxyphenyl isocyanate replaces tert-butylisocyanate, 1,2-dichloroethane is used as solvent instead of methylene chloride and the reaction is stirred at 50° C. for 18 hours. The final amine intermediate is provided as an oil.

The procedure for the synthesis of 3-[[(phenylamino)carbonyl]oxy]-1-aminoadamantane is essentially the procedure of 3-[[(tertbutylamino)carbonyl]oxy]-1-aminoadamantane except in the second step where an equivalent of phenyl isocyanate replaces the tert-butylisocyanate, 1,2-dichloroethane is used as solvent instead of methylene chloride and the reaction is stirred at 50° C. for 18 hours. The final amine intermediate is provided as a clear oil.

The procedure to make 2-aminoadamantane-5-ol is the same as in Example 1 except that the starting material is 2-aminoadamantane instead of 1-aminoadamantane.

The procedure for the synthesis of the nucleophile 3-acetoxy-1-aminoadamantane is essentially the procedure of 3-[[(tertbutylamino)carbonyl]oxy]-1-aminoadamantane except for a standard acylation of 1-benzylcarbamoyladamantane-3-ol using 1.2 eq of acetyl chloride, 3.0 eq. of pyridine, 0.1 eq of 4-dimethylaminopyridine and 1,2 dichloroethane which are all stirred at room temperature for 24 hours. The final amine is provided as a thick oil.

The procedure for the synthesis of 3-[[[(diisopropyl)amino]carbonyl]oxy]-1-amino-adamantane is essentially the procedure of 3-[[(tertbutylamino)carbonyl]oxy]-1-aminoadamantane except in the second step where an equivalent of diisopropylcarbamoyl chloride replaces the tert-butylisocyanate, 1,2-dichloroethane is used as solvent instead of methylene chloride and the reaction is stirred at 85° C. for 18 hours. The final amine intermediate is provided as a gray solid.

The procedure for the synthesis of 3-[[[(cyclohexyl)amino]carbonyl]oxy]-1-aminoadamantane is essentially the procedure of 3-[[(tertbutylamino)carbonyl]oxy]-1-aminoadamantane except in the second step where an equivalent of cyclohexylisocyanate replaces the tert-butylisocyanate, 1,2-dichloroethane is used as solvent instead of methylene chloride and the reaction is stirred at 50° C. for 18 hours.

The final amine intermediate is provided as a thick clear oil.

The procedure to make 3-ethoxy-1-adamantylamine (a clear oil) is the same as for 3-methoxy-1-adamantylamine except that iodoethane (1.3 equivalent) is used instead of iodomethane.

FORMULATION EXAMPLE

Tablets, each containing 50 mg of the active ingredient, NVP-BQS867, can be prepared as follows:
Composition (for 10,000 tablets)

| Active ingredient | 500.0 g |
| Lactose | 500.0 g |
| Potato starch | 352.0 g |
| Gelatin | |
| Talc | 60.0 g |
| Magnesium stearate | 10.0 g |
| Silica (highly disperse) | 20.0 g |
| Ethanol | q.s. |

The active ingredient is mixed with the lactose and 292 g of potato starch, and the mixture is moistened using an alcoholic solution of the gelatin and granulated by means of a sieve. After drying, the remainder of the potato starch, the talc, the magnesium stearate and the highly disperse silica are admixed and the mixture is compressed to give tablets of weight 145.0 mg each and active ingredient content 50.0 mg which, if desired, can be provided with breaking notches for finer adjustment of the dose.

III. EXAMPLE 2

Biological Experimental

List of abbreviations

| Abbreviation | Description |
|---|---|
| AMC | aminomethylcoumarin |
| BSA | bovine serum albumin |
| CHAPS | 3-((3-cholamidopropyl)-dimethylamino)-propanesulfonate |
| DABCYL | 4-((4-(dimethylamino)phenyl)azo)benzoic acid |
| DMSO | dimethylsulfoxide |
| DPP-2 | dipeptidyl peptidase 2 |
| DPP-8 | dipeptidyl peptidase 8 |
| DPP-9 | dipeptidyl peptidase 9 |
| DPP-IV | dipeptidyl peptidase IV |
| EDANS | 5-[(2-aminoethyl)amino]naphthalene-1-sulfonic acid |
| FAP | fibroblast activation protein, alpha |
| FI | fluorescence intensity |
| HCl | hydrochloric acid |
| HEPES | 4-(2-hydroxyethyl)-1-piperazineethanesulfonic acid |
| $M_W$ eff. | efficient molecular weight |
| Nle | norleucine |
| NVP-BQS867 | NVP-BQS867-NX-2 |
| PEP | prolyl-endopeptidase |
| prep. HPLC | preparative High-performance liquid chromatography |
| Rh110 | rhodamine-110 |
| SD | standard deviation |
| Tris | tris-(hydroxymethyl)-aminomethane |

IV. MATERIAL AND METHODS

A. A. Instrumentation

All protein and peptide containing solutions were handled in siliconized tubes (Life Systems Design, Merenschwand, Switzerland). The compound solutions as well as the enzyme and the substrate solutions were transferred to 384-well plates (black Cliniplate; cat. no. 95040020 Labsystems Oy, Finland) by means of a CyBi-Well 96-channel pipettor (CyBio AG, Jena, Germany).

1. 1. Instrumentation for FI Measurements

For fluorescence intensity (FI) measurements with AMC as dye, an Ultra Evolution reader (TECAN, Maennedorf, Switzerland) was used. The instrument was equipped with a combination of a 350 nm (20 nm bandwidth) and a 500 nm (25 nm bandwidth) bandpath filter for fluorescence excitation and emission acquisition, respectively. To increase the signal: background ratio, an appropriate dichroic mirror was employed. All filters and the dichroic mirror were purchased from TECAN.

FI measurements using a Rh110 dye were done with a Safire2 reader (TECAN, Maennedorf, Switzerland). The Safire2 is a monochomator-based instrument and wavelengths of 485 nm and 535 nm were taken for fluorescence excitation and emission acquisition, respectively. The bandwidths were set to 20 nm in both the excitation and the emission path.

The fluorophores in each well were excited by three flashes per measurement.

2. Calculation of $IC_{50}$ Values from Averaged Data

The data from the independent assay runs was averaged and plotted using program of Origin 7.5SR6 (OriginLab Corporation, Northampton, Mass., USA). Origin's built-in non-linear regression routine was used to fit the averaged data to the 'logistics' function $$y=A2+(A1-A2)/(1+(x/IC_{50})^p) \quad \text{(Equation 1)}$$

where y is the %-inhibition at the inhibitor concentration, x. A1 is the lowest inhibition value, i.e. 0%, and A2 the maximum inhibition value, i.e. 100%. The exponent, p, is the Hill coefficient.

B. Determination of $IC_{50}$ Values

For the determination of $IC_{50}$ values, the assays were performed at room temperature in 384-well plates. All final assay volumes were 30 μl. Test compounds were dissolved in 90% (v/v) DMSO/water and diluted in water (containing 0.05% (w/v) CHAPS) to 3-times the desired assay concentration.

For each assay, 10 μl water/CHAPS (±test compound) were added per well, followed by 10 μl protease solution (diluted with assay buffer; for final assay concentration cf. § Assay conditions). After 1 hour of incubation at room temperature, the reaction was started by addition of 10 μl substrate solution (for final concentrations cf. § Assay conditions). The eleven final compound concentrations were either 0.9 nM, 3 nM, 9 nM, 30 nM, 90 nM, 300 nM, 900 nM, 3 μM, 9 μM, 30 μM and 90 μM or 3 nM, 10 nM, 30 nM, 100 nM, 300 nM, 1 μM, 3 μM, 10 μM, 30 μM, 100 μM and 300 μM.

The effect of the compound on the enzymatic activity was obtained from the linear progress curves and determined from two readings, the first one taken directly after the addition of substrate (t=0 min) and the second one after 1 hour (t=60 min). The $IC_{50}$ value was calculated from the plot of percentage of inhibition vs. inhibitor concentration using non-linear regression analysis software (XLfit, Vers. 4.0; ID Business Solution Ltd., Guildford, Surrey, UK).

C. Assay Conditions

All conditions in respect to enzyme, substrate and buffer are listed below for the individual assays.

1.—DPP-2 (Dipeptidyl Peptidase 2)
enzyme: human DPP-2 covering amino acid 30-492; expressed in and purified from insect cells (baculovirus expression system)
substrate: Nle-Pro-AMC, purchased from Biosyntan (www.biosyntan.de), product number 4572
enzyme concentration: 0.03 nM
substrate concentration: 2 μM
assay buffer: 100 mM sodium citrate, pH 5.5, 0.05% (w/v) CHAPS 2.—DPP-IV (Dipeptidyl Peptidase IV)
enzyme: human DPP-IV covering amino acid 39-766; expressed in and purified from insect cells (baculovirus expression system)
substrate: Gly-Pro-AMC, purchased from Bachem (www.bachem.com), catalogue number 1-1225
enzyme concentration: 0.01 nM
substrate concentration: 10 μM
assay buffer: 25 mM Tris, pH 7.4, 140 mM NaCl, 10 mM KCl, 0.05% (w/v) CHAPS 3.—Human Plasma DPP-IV (Endogenous Dipeptidase IV in Human Blood Plasma)
enzyme: endogenous human DPP-IV from plasma sample, male donors
substrate: $(H-Ala-Pro)_2$—Rh110, in house synthesis
enzyme concentration: approx. 5 nM
substrate concentration: 10 μM
assay solution: human blood plasma, diluted to 50% plasma content with buffer (25 mM Tris, pH 7.4, 140 mM NaCl, 10 mM KCl, 0.05% (w/v) CHAPS)

4.—DPP-8 (Dipeptidyl-Peptidase 8)
enzyme: human DPP-8 covering amino acid 1-882; expressed in and purified from insect cells (baculovirus expression system)
substrate: Gly-Pro-AMC, purchased from Bachem (www.bachem.com), catalogue number 1-1225
enzyme concentration: 0.05 nM
substrate concentration: 10 μM
assay buffer: 25 mM Tris, pH 7.4, 140 mM NaCl, 10 mM KCl, 0.05% (w/v) CHAPS 5.—DPP-9 (Dipeptidyl-Peptidase 9)
enzyme: human DPP-9 covering amino acid 1-863; expressed in and purified from Pichia pastoris
substrate: Gly-Pro-AMC, purchased from Bachem (www.bachem.com), catalogue number 1-1225
enzyme concentration: 1 nM
substrate concentration: 10 μM
assay buffer: 25 mM Tris, pH 7.4, 140 mM NaCl, 10 mM KCl, 0.05% (w/v) CHAPS 6.—FAP (Fibroblast Activation Protein, Alpha)
enzyme: human FAPα covering amino acid 27-760 excluding the cytoplasmic and transmembrane domains; expressed in and purified from insect cells (baculovirus expression system)
substrate: Z-Gly-Pro-AMC, purchased from Bachem (www.bachem.com), catalogue number 1-1145
enzyme concentration: 0.1 nM
substrate concentration: 8 μM
assay buffer: 100 mM Tris, pH 7.4, 100 mM NaCl, 1 mM EDTA, 0.05% (w/v) CHAPS 7.—PEP (Prolyl-Endopeptidase)
enzyme: human PEP covering amino acid 1-710; expressed in and purified from Pichia pastoris
substrate: Z-Gly-Pro-AMC, purchased from Bachem (www.bachem.com), catalogue number 1-1145
enzyme concentrations: 0.03 nM
substrate concentration: 100 μM
assay buffer: 100 mM Tris, pH 7.4, 100 mM NaCl, 1 mM EDTA, 0.05% (w/v) CHAPS, 0.1% (w/v) BSA.

V. D. RESULTS

The results of all $IC_{50}$ measurements for the compound NVP-BQS867 are summarized in the Tables 3-1 to 3-7 below. For hDPP-IV, endogenous DPP-IV in human blood plasma, hDPP-8, hDPP-9, hFAP and hPEP.

TABLE V-1

(a) Potency of NVP-BQS867-NX-2 on human DPP-2.

| Experiment | $IC_{50}$ value [μM] | Hill coefficient | Mean $IC_{50}$ value ± SD [μM] |
|---|---|---|---|
| 1 | >300 | — | >90 |
| 2 | >300 | — | |
| 3 | >90 | — | |
| 4 | >90 | — | |

TABLE V-2

(b) Potency of NVP-BQS867-NX-2 on human DPP-IV.

| Experiment | $IC_{50}$ value [μM] | Hill coefficient | Mean $IC_{50}$ value ± SD [μM] |
|---|---|---|---|
| 1 | 0.004 | 0.7 | 0.006 ± 0.001 |
| 2 | 0.006 | 0.9 | |
| 3 | 0.007 | 1.3 | |
| 4 | 0.005 | 1.1 | |

TABLE V-3

(c) Potency of NVP-BQS867-NX-2 on human plasma DPP-IV.

| Experiment | $IC_{50}$ value [μM] | Hill coefficient | Mean $IC_{50}$ value ± SD [μM] |
|---|---|---|---|
| 1 | 0.003 | 1.4 | 0.004 ± 0.001 |
| 2 | 0.004 | 1.4 | |
| 3 | 0.004 | 1.2 | |
| 4 | 0.004 | 1.2 | |

TABLE V-4

(d) Potency of NVP-BQS867-NX-2 on human DPP-8.

| Experiment | IC$_{50}$ value [μM] | Hill coefficient | Mean IC$_{50}$ value ± SD [μM] |
|---|---|---|---|
| 1 | 8.3 | 1.2 | 8.0 ± 0.3 |
| 2 | 8.0 | 1.3 | |
| 3 | 8.1 | 1.2 | |
| 4 | 7.6 | 1.2 | |

TABLE V-5

(e) Potency of NVP-BQS867-NX-2 on human DPP-9.

| Experiment | IC$_{50}$ value [μM] | Hill coefficient | Mean IC$_{50}$ value ± SD [μM] |
|---|---|---|---|
| 1 | 0.7 | 1.0 | 0.5 ± 0.2 |
| 2 | 0.4 | 0.9 | |
| 3 | 0.6 | 1.0 | |
| 4 | 0.4 | 0.9 | |

TABLE V-6

(f) Potency of NVP-BQS867-NX-2 on human FAP.

| Experiment | IC$_{50}$ value [μM] | Hill coefficient | Mean IC$_{50}$ value ± SD [μM] |
|---|---|---|---|
| 1 | 43 | 1.3 | 24 ± 13 |
| 2 | 16 | 0.8 | |
| 3 | 19 | 0.7 | |
| 4 | 19 | 0.8 | |

TABLE V-7

(g) Potency of NVP-BQS867-NX-2 on human PEP.

| Experiment | IC$_{50}$ value [μM] | Hill coefficient | Mean IC$_{50}$ value ± SD [μM] |
|---|---|---|---|
| 1 | 52 | 0.7 | 25 ± 18 |
| 2 | 15 | 1.2 | |
| 3 | 18 | 0.8 | |
| 4 | 14 | 0.6 | |

What is claimed is:

1. A method of inhibiting dipeptidyl peptidase-IV comprising administering to a mammal in need of such treatment a therapeutically effective amount of a compound of formulae (I A), (I B), (X A), (X B), (Y A) or (Y B)

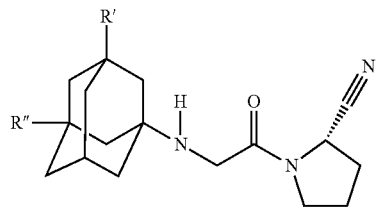

(IA)

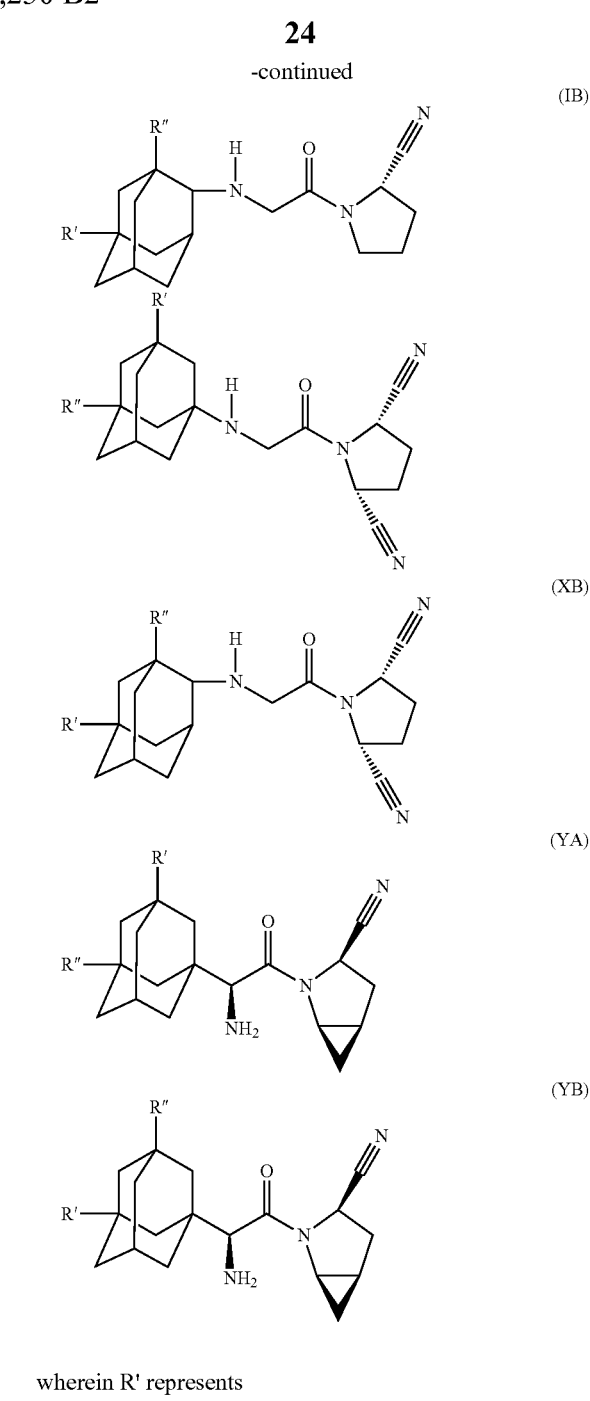

wherein R' represents and R" represents hydrogen, hydroxy, $C_1$-$C_7$alkoxy, $C_1$-$C_8$-alkanoyloxy, or $R_5R_4N$—CO—O—, where $R_4$ and $R_5$ independently are $C_1$-$C_7$alkyl or phenyl which is unsubstituted or substituted by a substitutent selected from $C_1$-$C_7$alkyl, $C_1$-$C_7$alkoxy, halogen and trifluoromethyl and where $R_4$ additionally is hydrogen; or $R_4$ and $R_5$ together represent $C_3$-$C_6$alkylene;

in free form of a pharmaceutically acceptable acid addition salt thereof.

2. A method of inhibiting dipeptidyl peptidase-IV comprising administering to a mammal in need of such treatment a therapeutically effective amount of a pharmaceutical composition comprising a therapeutically effective amount of the compound of formula (I A), (I B), (X A), (X B), (Y A) or (Y B) of claim 1 together with at least one pharmaceutically acceptable carrier or diluent.

3. The method according to claim 1 wherein the mammal in need of such treatment has non-insulin-dependent diabetes mellitus.

4. The method according to claim 2 wherein the mammal in need of such treatment has non-insulin-dependent diabetes mellitus.

* * * * *